(12) United States Patent
Scifert et al.

(10) Patent No.: US 9,931,435 B2
(45) Date of Patent: *Apr. 3, 2018

(54) MEDICAL IMPLANTS WITH RESERVOIR(S), AND MATERIALS PREPARABLE FROM SAME

(71) Applicant: Warsaw Orthopedic, Inc., Warsaw, IN (US)

(72) Inventors: Jeffrey L. Scifert, Arlington, TN (US); William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/137,188

(22) Filed: Apr. 25, 2016

(65) Prior Publication Data

US 2016/0310636 A1 Oct. 27, 2016

Related U.S. Application Data

(60) Continuation of application No. 14/226,463, filed on Mar. 26, 2014, now Pat. No. 9,320,708, which is a
(Continued)

(51) Int. Cl.
*A61K 9/70* (2006.01)
*A61L 27/24* (2006.01)
(Continued)

(52) U.S. Cl.
CPC ............... *A61L 27/24* (2013.01); *A61F 2/02* (2013.01); *A61K 9/0019* (2013.01);
(Continued)

(58) Field of Classification Search
CPC ..... A61K 9/0024; A61K 9/1652; A61L 27/24; A61L 27/58
See application file for complete search history.

(56) References Cited

U.S. PATENT DOCUMENTS 4,743,229 A 5/1988 Chu
4,775,890 A 10/1988 Chu
(Continued)

FOREIGN PATENT DOCUMENTS

WO WO 02/15881 2/2002
WO 2005004755 A1 1/2005
(Continued)

OTHER PUBLICATIONS

Internet pages, Healthcare Sales & marketing Network News: Kensey Nash Announces Launch of New Product . . . , http://salesandmarketingnetwork.com/news_release.php?ID=2005433 &key=Orthovita; 3 pages, last printed Nov. 1, 2005.
(Continued)

*Primary Examiner* — Carlos A Azpuru

(57) ABSTRACT

Described is a medically useful article comprising a three-dimensional body including one or more implantable substances, wherein the body defines one or more reservoirs for receiving amounts of a biocompatible wetting liquid. In certain embodiments the body is disruptable upon wetting with the biocompatible liquid to form a conformable implantable material such as a putty, paste or more flowable wetted implant material. Also described are methods for manufacturing such medical materials, and methods for using such medical materials to treat patients.

20 Claims, 1 Drawing Sheet

Related U.S. Application Data continuation of application No. 12/824,741, filed on Jun. 28, 2010, now Pat. No. 8,697,114, which is a division of application No. 11/404,202, filed on Apr. 14, 2006, now Pat. No. 7,824,703, which is a continuation-in-part of application No. 11/345,605, filed on Feb. 1, 2006, now Pat. No. 7,939,092.

(51) Int. Cl.

| | | |
|---|---|---|
| *A61K 9/00* | (2006.01) | |
| *A61K 9/16* | (2006.01) | |
| *A61L 27/58* | (2006.01) | |
| *A61L 24/00* | (2006.01) | |
| *A61L 24/10* | (2006.01) | |
| *A61L 27/46* | (2006.01) | |
| *A61F 2/02* | (2006.01) | |
| *A61L 24/02* | (2006.01) | |
| *A61L 27/02* | (2006.01) | |
| *A61L 27/54* | (2006.01) | |
| *A61L 27/56* | (2006.01) | |

(52) U.S. Cl.
CPC .......... *A61K 9/0024* (2013.01); *A61K 9/1652* (2013.01); *A61L 24/0015* (2013.01); *A61L 24/0036* (2013.01); *A61L 24/0042* (2013.01); *A61L 24/0084* (2013.01); *A61L 24/02* (2013.01); *A61L 24/10* (2013.01); *A61L 24/102* (2013.01); *A61L 27/02* (2013.01); *A61L 27/46* (2013.01); *A61L 27/54* (2013.01); *A61L 27/56* (2013.01); *A61L 27/58* (2013.01); *A61L 2300/112* (2013.01); *A61L 2300/252* (2013.01); *A61L 2300/412* (2013.01); *A61L 2300/414* (2013.01); *A61L 2300/45* (2013.01); *A61L 2300/604* (2013.01); *A61L 2400/06* (2013.01); *A61L 2430/02* (2013.01); *A61L 2430/38* (2013.01)

(56) References Cited

U.S. PATENT DOCUMENTS

| | | |
|---|---|---|
| 4,776,890 A | 10/1988 | Chu |
| 4,795,467 A | 1/1989 | Piez et al. |
| 4,992,226 A | 2/1991 | Piez et al. |
| 5,204,382 A | 4/1993 | Wallace et al. |
| 5,356,629 A | 10/1994 | Sander et al. |
| 5,425,770 A | 6/1995 | Piez et al. |
| 5,531,791 A | 7/1996 | Wolfinbarger, Jr. |
| 5,739,286 A | 4/1998 | Silver et al. |
| 5,925,736 A | 7/1999 | Neff et al. |
| 6,679,918 B1 | 1/2004 | Benedict et al. |
| 7,824,703 B2 * | 11/2010 | Scifert .............. A61L 24/0084 424/426 |
| 9,320,708 B2 * | 4/2016 | Scifert |
| 2002/0076429 A1 | 6/2002 | Wironen et al. |
| 2002/0082694 A1 | 6/2002 | McKay |
| 2002/0098222 A1 | 7/2002 | Wironen et al. |
| 2003/0236573 A1 | 12/2003 | Evans et al. |
| 2004/0002558 A1 | 1/2004 | McKay |
| 2004/0034434 A1 | 2/2004 | Evans et al. |
| 2004/0064193 A1 | 4/2004 | Evans et al. |
| 2004/0127987 A1 | 7/2004 | Evans et al. |
| 2004/0138758 A1 | 7/2004 | Evans et al. |
| 2004/0230309 A1 | 11/2004 | DeMauro et al. |
| 2005/0186240 A1 | 8/2005 | Ringeisen et al. |

FOREIGN PATENT DOCUMENTS

| | | |
|---|---|---|
| WO | WO 05/004755 | 1/2005 |
| WO | 2007090180 A1 | 8/2007 |
| WO | WO 2007/090180 | 8/2007 |

OTHER PUBLICATIONS

Internet pages, Orthovita Products: VITOSS Technical Specifications: Description, http://www.orthovita.com/products/vitoss/techspecs.html, 8 pages, last printed Nov. 1, 2005.
International Search Report and Written Opinion for PCT/US2007/064755 dated Nov. 6, 2007.

* cited by examiner

MEDICAL IMPLANTS WITH RESERVOIR(S), AND MATERIALS PREPARABLE FROM SAME

REFERENCE TO RELATED APPLICATION

The present application is a continuation application of U.S. patent application Ser. No. 14/226,463, filed on Mar. 26, 2014, which is a continuation application of U.S. patent application Ser. No. 12/824,741, filed Jun. 28, 2010, now U.S. Pat. No. 8,697,114, which is a divisional of U.S. patent application Ser. No. 11/404,202 filed Apr. 14, 2006, now U.S. Pat. No. 7,824,703, which is a continuation-in-part application of U.S. patent application Ser. No. 11/345,605, filed on Feb. 1, 2006, now U.S. Pat. No. 7,939,092. These entire disclosures are incorporated herein by reference into the present disclosure.

BACKGROUND OF THE INVENTION

The present invention relates generally to medical implants, and in certain aspects to conformable medical materials such as putties or pastes, and articles and methods useful for preparing such conformable medical materials.

A variety of materials have been suggested for the treatment of bone and other tissue defects. For example, wetted implant materials such as medical putties, pastes, or more flowable materials have been suggested for treating tissue defects, especially for their capacity for introduction into tissues and in some cases their ability to conform to the shape of defects. Several general techniques for providing the wetted implant material in the operating environment are known. For example, the conformable material can be provided by the manufacturer in a pre-wetted state in a syringe or other container. In addition, it is known to provide a sterile, dry material that can be wetted with a sterile liquid at or about the time of use. In these latter instances, relatively little emphasis has been given to the manner in which the liquid is combined with the dry material, or to rendering this operation more convenient or efficient.

In view of the background in the area, there exist needs for improved and/or alternative medical materials and methods for their manufacture and use. In certain of its aspects, the present invention is directed to these needs.

SUMMARY OF THE INVENTION

Accordingly, in certain aspects, the present invention features novel implant material structures that include adaptations that are useful for retaining amounts of liquid that are charged to the structure in order to wet the structure. Such adaptations can be incorporated into articles formed of implantable material(s) in a manner that allows the liquid to pool in contact with the structure to provide time for the liquid to be absorbed. Thus, in one embodiment, the present invention is directed to a medical article comprising a three-dimensional body formed of an implantable medical material. The three-dimensional body is wettable with a biocompatible liquid, and is disruptable upon wetting with the biocompatible liquid so as to form a disrupted, wetted implant material. The three-dimensional body defines one or more reservoirs for receiving the biocompatible liquid.

In another aspect, the invention provides a method for making a medical material comprising providing a three-dimensional body formed of an implantable material, the three-dimensional body defining one or more reservoirs for receiving a biocompatible liquid. The method also includes delivering a biocompatible liquid into the at least one reservoir, and disrupting the body to form an implantable material.

In another aspect, the invention provides a method for manufacturing a medical article, comprising forming a disruptable three-dimensional body including an implantable material, and providing in the three-dimensional body one or more reservoirs for receiving a biocompatible liquid. The reservoir(s) can, for instance, be provided in the body upon formation of the body, or after formation of the body.

In another aspect, the invention provides a medical article including a three-dimensional body formed of an implantable material. The three-dimensional body defines one or more reservoirs configured to receive and pool a liquid wetting medium for the body. In certain forms, the implant body displays delayed absorption of aqueous liquids such as isotonic saline. For example, the implant body can be of such a nature that when immersed in isotonic saline at 25° C., it takes at least about 5 seconds for the body to be completely saturated with the isotonic saline. Alternatively or in addition, the implant body can be of such a nature that when the reservoir(s) defined by the body are rapidly filled with isotonic saline at 25° C., the isotonic saline pools in the reservoir(s) and thereafter takes at least about 5 seconds to completely soak into the body.

In another aspect, the invention provides a method for preparing a wetted medical implant body. The method includes the steps of providing a three-dimensional body formed of an implantable material, the three-dimensional body defining one or more reservoirs. A biocompatible liquid wetting medium is charged to the one or more reservoirs so as to pool in the one or more reservoirs, and is thereafter completely absorbed by the body.

In another aspect, the invention provides a kit useful for preparing an implantable medical material, the kit including three-dimensional body comprising an implantable material, the three-dimensional, body defining one or more reservoirs for receiving a biocompatible liquid. In desired embodiments, the body is disruptable. The kit also includes an amount of a biocompatible liquid for wetting the three-dimensional body.

In still other aspects, the present invention provides methods for treating patients using articles and/or conformable materials described or prepared as described herein.

Additional embodiments as well as features and advantages of the present invention will be apparent to those of ordinary skill in the art from the descriptions herein.

DETAILED DESCRIPTION

Figure 1:
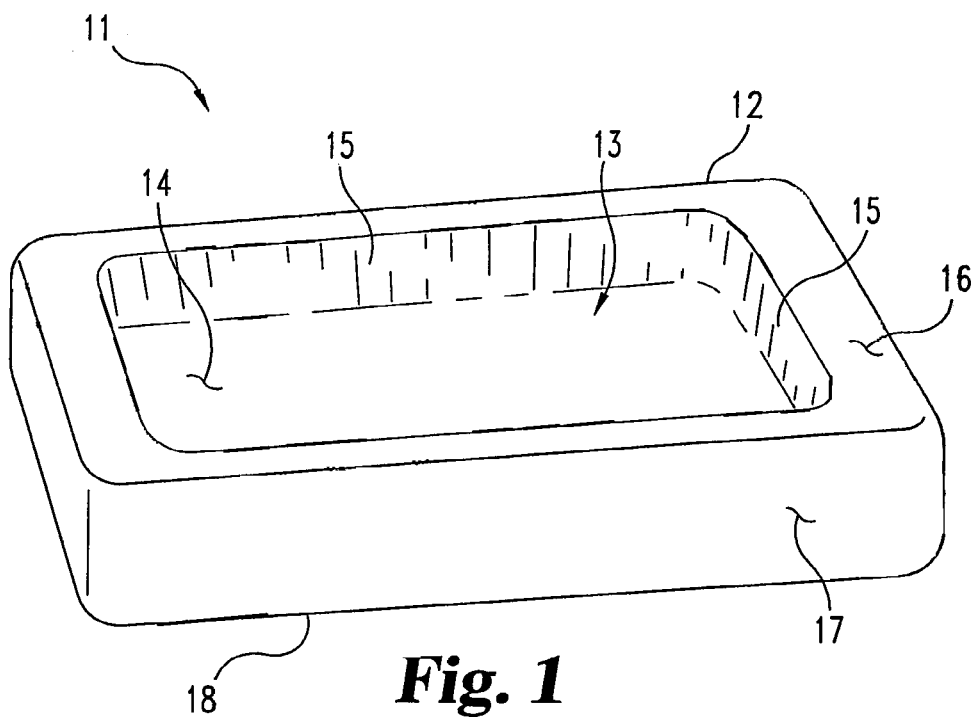
FIG. 1 provides a perspective view of an implant material body of the invention including a reservoir for receipt of wetting liquid.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, in certain aspects, the present invention relates to implantable medical materials, and to articles and methods for making and using implantable medical materials. In particular embodiments, the present invention provides medical articles that include a three-dimensional body formed with one or more implantable materials, wherein the body is of such a nature that it can be readily disrupted and broken down into a conformable substance, such as a putty or paste, upon wetting with a biocompatible liquid, and wherein the body is so configured as to allow a biocompatible liquid to pool in contact with the body. In this manner, in situations in which the body cannot absorb a biocompatible liquid as quickly as it is charged to the body, amounts of the liquid can be allowed to pool and will be held by the body until they are absorbed. Such situations may arise, for example, where the body is insufficiently porous to immediately absorb all of the charged liquid, and/or where the body exhibits other characteristics which participate in resisting immediate absorption of liquids applied to its surface, such as the composition of the body relative to the wetting liquid (e.g. in terms of their hydrophilic and/or hydrophobic character or extent thereof), the existence of film layers or other relatively flow-resistant features on surfaces of the body, and/or other factors. Delayed absorption of wetting liquids can also occur in non-disruptable three-dimensional bodies, such as dimensionally-stable sponge devices exhibiting shape memory that are not susceptible in the wetted condition to manual crushing and kneading to form a putty or other conformable material, but rather are sustained as a single, integral piece. In accordance with aspects of the present invention, one or more reservoirs can be incorporated into such dimensionally-stable sponge or other devices to facilitate the wetting operation.

However, in advantageous forms of the invention, a medical article is provided having a body that will exhibit a disruptable character such that it can be broken down by physical manipulation (e.g. manual crushing and kneading) when combined with a liquid. Upon such manipulation, the formed material will exhibit a more conformable character than the original body, such as that provided by a putty, paste or more flowable form, depending for instance upon the amount of liquid combined with a given amount of body material solids. In certain desirable embodiments, the conformable material formed upon wetting and disruption of the body will be a putty exhibiting a combination of advantageous properties including malleability, cohesiveness, and shape retention.

In this regard, as used herein the term "malleable" means that the material is capable of being permanently converted from a first shape to a second shape by the application of pressure. The term "cohesive" as used herein means that the putty tends to remain a singular, connected mass upon stretching, including the exhibition of the ability to elongate substantially without breaking upon stretching. In the context of putties of the invention containing insoluble collagen fibers or another natural or synthetic fibrous material, upon stretching, the advantageous putties exhibit elongation, during which the existence of substantial levels of intermeshed fibers clinging to one another becomes apparent. As used herein, the term "shape-retaining" means that a putty material is highly viscous and unless acted upon with pressure tends to remain in the shape in which it is placed. On the other hand, thinner paste form materials in accordance with the invention flow more readily than putties, and thus tend to deform substantially under the force of gravity (e.g. pool or puddle) upon application to a surface. Further, low-viscosity, highly flowable (e.g. injectable) materials may also be prepared from articles in accordance with the invention.

The medical articles of the invention can comprise any suitable implantable material, desirably at least one biodegradable material. In certain specific embodiments, the medical article will be composed entirely of one or more biodegradable materials. Suitable materials for use in the invention include, for example, natural polymers such as polysaccharides, proteins and polypeptides, glycosaminoglycans, proteoglycans, collagen, elastin, hyaluronic acid, dermatan sulfate, chitin, chitosan, pectin, (modified) dextran, (modified) starch, or mixtures or composites thereof. Synthetic polymers may also be employed, including for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethyleneglycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, etc., that can be polymerized from the monomers related to previously-listed homo- and copolymers. It will be well understood that these and other implantable materials, or combinations thereof, may be used in aspects of the present invention.

Fibrous materials, including fibrous protein materials, can be used in implantable materials of the present invention. These include, as examples, fibers comprising collagen, elastin, fibronectin, laminin, or other similar structural, fiber-forming proteins. Insoluble, fibrous demineralized bone matrix (DBM) materials can also be used in the invention, alone or in combination with other fibrous materials disclosed herein.

In certain embodiments, the implantable material of the three-dimensional body will include one or more agents that form a gel upon combination with a biocompatible liquid, e.g. after being solubilized by the biocompatible liquid. Suitable gel-forming agents for these purposes include, for instance: plant extracts such as agar, ispaghula, psyllium, cydonia or ceratonia; vegetable oils such as hydrogenated castor oil; gums such as guar gum, acacia gum, ghatti gum, karaya gum, tragacanth gum or xanthan gum; synthetic and natural polysaccharides such as alkylcelluloses, hydroxyalkylcelluloses, cellulose ethers, cellulose esters, nitrocelluloses, dextrin, agar, carrageenan, pectin, furcellaran or starch or starch derivatives such as sodium starch glycolate; polysaccharides such as agar and carrageenan; polypeptides such as zein, gelatin, soluble collagen and polygeline; or mixtures of two or more of any of these or other suitable gel-forming agents. Further, in some variants of the invention, a gel-forming agent that is soluble in the biocompatible wetting liquid will be used in combination with another implantable material that is insoluble in the biocompatible liquid, e.g. an insoluble fibrous material as discussed above, to ultimately form a paste, putty or more flowable wetted implant material comprising insoluble fibers suspended or mixed with a gel substance.

In some forms, the putty or other wetted, conformable implant material of the invention contains both insoluble collagen fibers and soluble collagen. The soluble collagen and insoluble collagen fibers can first be prepared separately, and then combined. Both the soluble collagen and the insoluble collagen fibers can be derived from bovine hides, but can also be prepared from other collagen sources (e.g. bovine tendon, porcine tissues, recombinant DNA techniques, fermentation, etc.). Suitable collagen materials for use in the invention can be prepared using these or other techniques known in the literature or can be obtained from commercial sources, including for example from Kensey Nash Corporation (Exton, Pa.) which manufactures soluble collagen known as Semed S, fibrous collagen known as Semed F, and a composite collagen known as P1076. Naturally-derived human collagen or recombinant human collagen can also be used in the present invention.

The implant materials of the invention can also include a mineral component. The mineral used can include a natural or synthetic mineral that is effective to provide a scaffold for bone ingrowth. Illustratively, the mineral matrix may be selected from one or more materials from the group consisting of bone particles, Bioglass®, tricalcium phosphate, biphasic calcium phosphate, hydroxyapatite, corraline hydroxyapatite, and biocompatible ceramics. Biphasic calcium phosphate is a particularly desirable synthetic ceramic for use in the invention. Such biphasic calcium phosphate can have a tricalcium phosphate:hydroxyapatite weight ratio of about 50:50 to about 95:5, more preferably about 70:30 to about 95:5, even more preferably about 80:20 to about 90:10, and most preferably about 85:15. The mineral material can be particulate having an average particle diameter between about 0.4 and 5.0 mm, more typically between about 0.4 and 3.0 mm, and desirably between about 0.4 and 2.0 mm.

In another aspect of the invention, the mineral material can include bone particles, possibly cancellous but preferably cortical, ground to provide an average particle diameter among those discussed above for the particulate mineral material. Both human and non-human sources of bone are suitable for use in the instant invention, and the bone may be autographic, allographic or xenographic in nature relative to the mammal to receive the implant. Appropriate pre-treatments known in the art may be used to minimize the risks of disease transmission and/or immunogenic reaction when using bone particles as or in the mineral material.

In one embodiment, xenogenic bone that has been pre-treated to reduce or remove its immunogenicity is used in or as the porous mineral matrix in the implant composition. For example, the bone can be calcined or deproteinized to reduce the risks of immunogenic reactions to the implant material.

Bioactive agents can be delivered with implant materials of the invention. These agents can be incorporated into the three-dimensional body upon its formation, and/or can be added later, for example during (e.g. as incorporated in a wetting agent) or after the formation of a wetted, conformable implant composition from the body. Such bioactive agents include, but are not limited to, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenlcs, non-steroidal anti-inflammatory agents, steroidal anti-inflammatory agents, antioxidants, vaso-active agents, bone-active agents, osteogenic factors, antiarthritics, and diagnostic agents.

Bioactive agents may also be provided by tissue materials, including for instance autologous tissue materials, which are incorporated into the material to be implanted in the patient. Such tissue materials can include blood or blood fractions, bone marrow or bone marrow fractions, and/or other sources of cells or other beneficial tissue components derived from the patient to be treated or another suitable animal source.

Bioactive agents such as those described herein can be incorporated homogeneously or regionally into an implantable material by simple admixture or otherwise, and/or may be incorporated into a three-dimensional implant body and/or a final wetted (preferably conformable) medical material in conjunction with another carrier form or medium such as microspheres or another microparticulate formulation. Suitable techniques for forming microparticles are well known in the art, and can be used to entrain or encapsulate bioactive agents, whereafter the microparticles can be dispersed within the implantable material upon forming the three-dimensional body and/or upon wetting the body (e.g. by incorporating the microparticles in the wetting liquid).

The implant material bodies in accordance with the invention can be provided in any suitable shape, including cylinders, cubes, irregular or other shapes, having one or more reservoirs defined therein for receiving amounts of a wetting liquid, e.g. to be used in the preparation of a wetted implant body or a wetted malleable formulation such as a putty, paste, or more flowable substance from the implant material body. Similarly, the reservoir(s) defined in implant bodies of the invention can have any suitable shape, including irregular cross-sectional shape or regular cross-sectional shapes such as rectangular, square, circular, ovoid, or other suitable shapes. Where multiple reservoirs are defined by the body, they can all occur on a single face of the body, or they may separately occur on two or more different faces of the body.

The implant material bodies of the present invention can be prepared using any suitable technique, including for example by casting a liquid medium into which the dry ingredients have been added, and then drying that medium by any appropriate means such as air drying or lyophilization. In many instances, such cast, dried bodies form surface features that tend to initially resist the absorption of liquids such as aqueous mediums. Other known preparative techniques such as molding, extrusion, machining, and the like, can also be used in the preparation of implant material bodies of the invention.

With reference to FIG. 1, depicted is one illustrative, dried porous implant body 11 of the invention. The body 11 has a cast material 12 which defines a reservoir 13. The reservoir 13 has a bottom surface 14 and side walls 15, and can hold a liquid to be used to wet the body 11 in the formation of a putty, such that the liquid can be conveniently charged to reservoir 13 and allowed to soak into body 11 over time. The body 11 has an upper surface 16 surrounding the reservoir 13, as well as sidewalls 17 and a bottom surface 18. In use, a liquid can be charged to the reservoir, for example using a syringe, and allowed to soak into the body 11. The liquid can be charged quickly such that amounts of the liquid pool in the reservoir, and thereafter soak into the body over a period of time.

Figure 2:
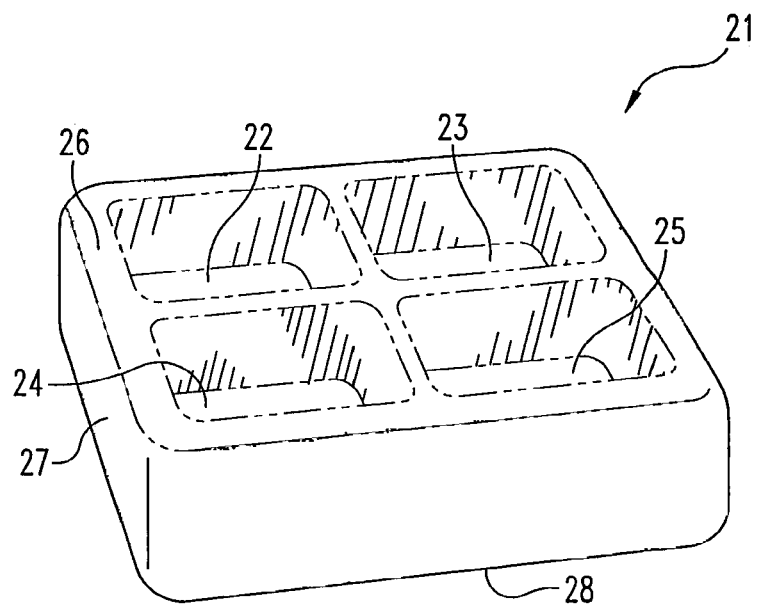
FIG. 2 provides a perspective view of an implant material body of the invention including a plurality of reservoirs for receipt of wetting liquid.

Referring now to FIG. 2, shown is another implant body 21 of the present invention. Implant body 21 includes a plurality of reservoirs 22, 23, 24 and 25 defined therein. The body 21 has an upper surface 26 defined around the reservoirs 22-25, as well as sidewalls 27 and a bottom surface 28. In use, one or more biocompatible liquids can be charged to one, some or all of reservoirs 22-25, and allowed to soak into the implant body 21.

In certain embodiments, the body (e.g. 11, 21) will exhibit a disruptable character, such that it can be broken down by physical manipulation (e.g. manual crushing and kneading) to form a paste, putty or other flowable material when combined with a liquid. Thus, in these embodiments, chemical, covalent crosslinking between the materials formed in the shape of the body, if any, will generally be minimal. Other modes of providing integrity to the body (11, 21) can be used, e.g. dehydrothermal crosslinking, or crosslinking or adhesive forces imparted by ionic or hydrogen bonding. It will thus be understood that crosslinking can be present in the body (11, 21), but that it will be of such a nature to leave the body disruptable to form a putty or other conformable wetted implant material as described herein. In certain forms, the body (e.g. 11, 21) will be a relatively inelastic, breakable and/or friable material that will exhibit essentially no shape memory in the dry and/or in the wetted condition. Thus, in such forms of the invention, upon crushing a region of the implant body, that region will exhibit substantially no ability to return to its original shape. Such disruptable bodies can be implanted as-is after wetting without being manipulated to form the paste, putty or other conformable material; however, in preferred modes of use, the wetted, disruptable body will be converted to such conformable materials prior to implantation.

Typically, in situations wherein a disruptable implant body (e.g. 11, 21) is relatively highly porous, the combination of the body with the liquid carrier, and the physical kneading or other mixing of the resultant mass, will result in a reduction of the volume of the body, for example resulting in a putty, paste or more conformable material volume that is about 30% to about 70% of that of the original implant body, and in certain instances about 40% to about 60%. This is a result of a breakdown of the original porosity of the implant body to form a relatively less porous or non-porous putty, paste or other conformable implant composition. It will be understood, however, that the volume of the prepared, conformable implant material can exceed that of the original implant body. For example, where a highly flowable implant material is to be prepared from a relatively porous body, the amount of liquid material combined with the implant material body may be relatively high and sufficient to result in an implantable material having a volume matching or exceeding that of the original body. Additionally, where the implant body has a low porosity or is substantially non-porous, the addition and mixing of the wetting liquid with the body can result in a wetted implant material volume that is greater than that of the original implant body. These and other variants of the invention will be well understood by those skilled in the art in view of the teachings herein.

The biocompatible liquid will often be an aqueous substance, including for instance sterile water, physiological saline, blood, bone marrow, bone marrow fractions or other solutions (with or without organic co-solvents), emulsions or suspensions that provide adequate wetting characteristics to form putties, pastes or other conformable materials of the invention. Biocompatible organic liquids can also be used in the present invention, alone or in conjunction with water, to provide biocompatible liquids for addition to the implant body.

In certain uses, a disruptable implant body (e.g. 11, 21) of the invention such as a dried, porous body can be combined with a sufficient amount of the biocompatible liquid material to prepare a putty, paste, flowable or otherwise conformable form material. In some modes of use, the liquid material will be added to the reservoir(s) of the body and will pool therein and stand for some period of time as amounts of the liquid material are soaked into the bodies. In this manner, the liquid material can be charged more quickly and conveniently into contact with the bodies, with enhanced assurance that all of the charged liquid will soak into the body as opposed to running off of the body onto adjacent surfaces, etc. This provides greater assurance that the bodies and ultimate prepared formulations will be wetted to the desired extent, and/or that amounts of the liquid material will not be lost in the transfer. This can be especially important in situations in which the liquid material contains one or more bioactive agents, and the dosing of the agent to the patient needs to be carefully controlled.

Pursuant to certain aspects of the invention, the implant material body will define at least one reservoir suitable for receiving and holding a substantial volume of a biocompatible liquid. The volume of the reservoir(s) can vary in accordance with the volume of implant material incorporated in the body and other factors, and in some embodiments of the invention the reservoir(s) will have a volume of at least about 1 cubic centimeter (cc), at least about 3 cc, or at least about 5 cc. These volumes can be provided by a single reservoir as illustrated in FIG. 1, or by multiple reservoirs as illustrated in FIG. 2. Illustratively, such volumes can be defined by 1 to about 20 defined reservoirs, or 1 to about 10 reservoirs.

In additional forms of the invention, the volume of the reservoir(s) can represent a substantial ratio when considered relative to the volume defined by the external contour of the body. In certain embodiments, the volumetric ratio of the reservoir(s) to the body is at least about 1:10, at least about 1:5, or at least about 1:3. In large reservoir(s) embodiments, the volumetric ratio of the reservoir(s) to the body can be at least about 1:2, or at least about 1:1. Reservoir(s) to body volumetric ratios of greater than 1:1 are also possible in accordance with the invention. Again, these volumetric ratios can be provided by a single defined reservoir or a plurality of defined reservoirs. Illustratively, such volumetric ratios can be defined by 1 to about 20 reservoirs, or 1 to about 10 reservoirs.

In particular embodiments of the invention, the implant material body occupies a volume of about 1 cc up to about 50 cc and includes a single reservoir or a plurality of reservoirs having a total volume of about 1 cc to about 50 cc, with the volumetric ratio of the reservoir(s) to the body being in the range of about 1:5 to about 2:1. In other embodiments, the body occupies of volume of about 3 cc to about 30 cc and defines a single reservoir or a plurality of reservoirs having a total volume of about 3 cc to about 30 cc, with the volumetric ratio of the reservoir(s) to the body being in the range of about 1:2 to about 2:1. In specific embodiments of those discussed above, the volumetric ratio of the reservoir(s) to the body can be in the range of about 1:1.5 to about 1.5:1.

The volume of the reservoir(s) in the implant material body can be sufficient to accommodate an amount of a liquid wetting agent selected to provide the desired consistency to the final, wetted implant material, e.g. giving the wetted material a putty, paste or more flowable character. Alternatively, the reservoir(s) can be sized having insufficient volume to accommodate the selected amount of wetting agent to be added, and multiple charges can be made to the reservoir(s) while allowing a period of time in between charges for the prior-charged liquid to partially or completely soak into the body. In addition, the reservoirs can provide or incorporate one or more indicia that correlate to a desired volume of wetting agent for addition to the implant body. For example, the reservoir(s) may be sized such that when quickly filled to capacity, the desired amount of wetting agent will have been added to the implant body, with the wetting agent thereafter soaking into the body over time. Alternatively, ledges, score marks or other indicia may be defined in or around walls of the reservoir to provide indicia of an amount of fluid added to the implant body. Still further, where a disruptable implant body defines more than one reservoir, the reservoirs may provide a reliable way to wet the implant body to differing extents and thereby result in wetted implant materials of differing, selected consistencies, depending upon how many reservoirs are charged to capacity (or to another indicia) with the wetting liquid. Thus, only a single or relatively few provided reservoir(s) can be charged with liquid to result (e.g. after kneading) in a controlled, thicker putty-like material, whereas relatively more reservoirs can be charged with liquid in the event that a controlled, thinner paste or more flowable material is ultimately desired. Thus, a single style of implant body in accordance with the invention can be used to prepare final formulations of varying consistency and/or wetted bodies of varying levels of saturation. These and other similar variations are contemplated as forming a part of the present invention.

The total amount of wetting agent applied to the implant material body will typically depend upon the properties desired of the final implant material. For example, in the case of conformable implant materials, the final implant material may be a lightly wetted solid mass, a putty, a paste, or a more flowable liquid implant material such as an injectable material. In many cases, the wetting liquid will be added in sufficient amount to constitute about 20% to about 95% by weight of the final implant material, more typically about 40% to about 80% by weight, and in certain embodiments about 50% to about 75% by weight. It will be understood, however, that other amounts can also be used within broader aspects of the present invention.

In certain embodiments of the invention, the implant body defining the reservoir(s) will exhibit relatively slow sorptivity for the biocompatible liquid to be used to wet the body. Thus, when an amount of the liquid is quickly charged (e.g. in less than about 2 seconds) to the reservoir(s), a substantial amount of the liquid will pool in the reservoir(s), and thereafter eventually soak into the body. Specific embodiments of the invention pertain to such implant bodies which exhibit delayed absorption of aqueous liquids. For example, the implant body can be of such a nature that when immersed just below the surface in isotonic saline at 25° C., it takes at least about 5 seconds for the body to be completely saturated with the isotonic saline. In some forms, such time to saturation when immersed in isotonic saline water will be at least about 10 seconds, or even at least about 1 minute. Alternatively or in addition, the implant body can define one or more reservoir(s), for example having volume(s) as specified hereinabove, that when quickly filled (e.g. in less than about 2 seconds) with isotonic saline at 25° C. result in the pooling of the isotonic saline in the reservoir(s), after which it takes at least about 5 seconds for all of the saline to soak into the body, in certain embodiments at least about 10 seconds, and in some embodiments at least about 1 minute, e.g. from about 1 minute to about 20 minutes. It will be understood that these features relating to the rate of liquid sorption or rate of liquid charge are characteristic of certain embodiments, but are not necessary to all aspects of the present invention.

In still further embodiments, the present invention provides methods for treating patients that involve implanting in the patients a medical implant material as described herein. In such uses, an implant material of the invention can be implanted at a site at which tissue growth is desired, e.g. to treat a disease, defect or location of trauma, and/or in some instances to promote artificial arthrodesis. The medical compositions can be used as or in surgical implants at, in, on, or near bone defect sites, cartilage repair sites, or other musculoskeletal sites. Alternatively, the compositions of the invention may be applied to larger segments of bone, artificial implants, or any other kind of surgical implant. In certain embodiments, the conformable character of the compositions enables their positioning, shaping and/or molding within voids, defects or other areas in which new tissue growth is desired, and/or in which the delivery of a bioactive agent is desired. In particularly advantageous embodiments, a conformable material will be a putty having shape-retaining properties that desirably provide sufficient three-dimensional integrity to resist substantial compression when impinged by adjacent soft tissues of the body at a bony implant site.

Illustrative bone repair sites that can be treated with medical compositions of the invention include, for instance, those resulting from injury, defects brought about during the course of surgery, infection, malignancy or developmental malformation. The putty compositions can be used in a wide variety of orthopedic, periodontal, neurosurgical and oral and maxillofacial surgical procedures including, but not limited to: the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the isolate or implant comprising the isolate include, but are not limited to: the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

Illustrative cartilage repair sites that can be treated with medical compositions of the invention include, as examples, articular cartilage surfaces occurring in articular joints having at least two major bones. Examples include, but are not limited to the elbow, wrist, phalanx, knee, and ankle. Additionally, cartilage surfaces within shoulder and hip joints can be treated.

The present invention also provides medical kits that can be used to prepare implant materials. Such kits can include a implant material body according to the invention, along with an aqueous medium or other biocompatible wetting liquid for combination with the body, e.g. in some cases to form a conformable wetted material, and/or another item such as a load-bearing implant (e.g. a spinal spacer), and/or a transfer device such as a syringe, and/or a therapeutic substance, for example an osteogenic substance such as a BMP. In one specific form, such a medical kit will include a dried, porous body defining one or more reservoirs, a BMP in lyophilized form (e.g. rhBMP-2), and an aqueous medium for reconstitution of the BMP to prepare an aqueous formulation that can then be added to the reservoir(s) in the process of providing a wetted body for implantation, or of preparing an osteogenic putty, paste or other conformable implant material of the invention.

In select forms, the present invention provides novel implantable conformable compositions, and articles and methods for preparing them, which include an amount of a biocompatible liquid, an amount of a particulate mineral material, an amount of a resorbable fiber material that is insoluble in the biocompatible liquid, and an amount of a gel forming agent that is soluble in the biocompatible liquid, wherein the resorbable fiber material is incorporated at a level significantly higher than the gel-forming agent on a weight to weight (dry) basis. It is contemplated that such advantageous embodiments disclosed herein form a part of the disclosed invention, whether or not the article or implant body from which the conformable composition is prepared defines a reservoir(s). Such novel combinations of ingredients provide a medical putty material that not only contains a significant, high level of large particulate mineral, but also can exhibits superior properties in handling and/or implantation.

Selected putties according to these aspects of the present invention can include a combination of soluble collagen as a gel-forming agent, and insoluble collagen fibers. "Soluble collagen" refers to the solubility of individual tropocollagen molecules in acidic aqueous environments. Tropocollagen may be considered the monomeric unit of collagen fibers and its triple helix structure is well recognized. "Insoluble collagen" as used herein refers to collagen that cannot be dissolved in an aqueous alkaline or in any inorganic salt solution without chemical modification, and includes for example hides, splits and other mammalian or reptilian coverings. For example, "natural insoluble collagen" can be derived from the corium, which is the intermediate layer of an animal hide (e.g. bovine, porcine, etc.) that is situated between the grain and the flesh sides. "Reconstituted collagen" is essentially collagen fiber segments that have been depolymerized into individual triple helical molecules, then exposed to solution and then reassembled into fibril-like forms.

In accordance with certain features of the invention, the medical article and subsequent processing thereof are arranged to provide a malleable, cohesive, shape-retaining putty that includes a combination of mineral particles and an organic carrier (e.g. collagen), wherein the organic carrier includes insoluble fibers, for example collagen fibers, and an equal or relatively lesser amount by weight of a soluble gel-forming agent, for example soluble collagen. In one embodiment, an implantable medical material is provided in the form of a malleable, cohesive, shape-retaining putty comprised 60% to 75% by weight of a liquid medium such as an aqueous liquid medium, and dispersed mineral particles having an average particle diameter in the range of 0.4 mm to 5 mm at a level of at least about 0.25 g/cc, more typically in the range of about 0.25 g/cc to about 0.35 g/cc. The putty also includes an insoluble fiber material (e.g. collagen or another fiber material as disclosed above) at a level of 0.04 g/cc to 0.1 g/cc, and a soluble gel forming agent (e.g. soluble collagen or another gel-forming agent as disclosed above) at a level of 0.01 g/cc to 0.08 g/cc, with the proviso that the weight ratio of the insoluble fibers to soluble gel-forming agent is in the range of 4:1 to 1:1. Such a putty can be used as an osteoconductive or other tissue conductive material, for example in bone void filler applications. Alternatively, such a putty can incorporate one or more bioactive factors. In preferred embodiments, such a putty incorporates one or more osteogenic proteins to provide an osteogenic putty. Illustratively, malleable, cohesive, shape-retaining, osteogenic putties can comprise a bone morphogenic protein incorporated therein in an effective amount to render the putty osteogenic when implanted in a mammal, such as a human patient. In one embodiment, an inventive putty composition includes bone morphogenic protein at a level of about 0.6 milligrams per cubic centimeter (mg/cc) of putty to about 2 mg/cc of putty, advantageously at a level of about 0.8 mg/cc to about 1.8 mg/cc.

Methods for preparing such an implantable medical putty material can include providing a dry, porous material that includes a particulate mineral material having an average particle diameter of about 0.4 mm to about 5 mm embedded within a disruptable matrix. The dry material can optionally define one or more reservoirs as described herein, and be comprised about 70% to about 90% by weight of the particulate ceramic material and 10% to 30% by weight of the insoluble fiber material and gel-forming agent. The dry material includes insoluble fibers and soluble gel-forming agent in a weight ratio of 4:1 to 1:1, advantageously about 75:25 to about 60:40. In still further embodiments, the weight ratio of insoluble fibers to gel-forming agent in the dry material will be about 75:25 to about 65:35, and in one specific embodiment about 70:30. An amount of an aqueous medium or other suitable biocompatible liquid medium is added to the dry material, e.g. by charging the liquid medium to the one or more reservoirs when present, and the dry material body is disrupted so as to prepare a malleable, cohesive, shape-retaining putty that comprises 60% to 75% by weight of liquid. In certain variations of such embodiments, an aqueous medium can be used that includes a bone morphogenic protein dissolved therein at a level of about 0.6 mg/cc to about 2 mg/cc, so as to result in an implantable osteogenic medical material.

In particular inventive embodiments, the three-dimensional body will be composed of a dried implant material formed into a porous body that includes a particulate mineral material having an average particle diameter of about 0.4 mm to about 5.0 mm embedded within a collagenous matrix, desirably a disruptable collagenous matrix. The dried, porous implant material will be comprised 70% to 90% by weight of the particulate mineral material and 10% to 30% by weight of collagen. The collagenous matrix can include insoluble collagen fibers and soluble collagen present in a weight ratio as discussed above, that is, 4:1 to 1:1, advantageously about 75:25 to about 60:40, more advantageously about 75:25 to about 65:35, and in one specific embodiment about 70:30. In addition, as discussed above, the particulate mineral material will typically have an average particle diameter between 0.4 and 3.0 mm, and more desirably between 0.4 and 2.0 mm.

The dried, porous or other three-dimensional body can have a density of between about 0.1 g/cc to about 0.3 g/cc, more desirably between about 0.15 g/cc and about 0.25 g/cc, and in certain aspects between about 0.18 g/cc and about 0.25 g/cc. Such implant bodies can also exhibit porosities of at least about 50%, more desirably at least about 70% up to about 90%, and in certain embodiments in the range of about 80% to about 90%.

Once in place, an osteogenic putty or other implant material of the invention can be effective to induce and support the ingrowth of bone into the desired area even in a primate subject such as a human exhibiting a relatively slow rate of bone formation compared to smaller mammals, for example rodents or rabbits.

Osteogenic materials of the invention are especially advantageous when used in bones or bone portions that are vascularized to only moderate or low levels. These areas present particularly low rates of bone formation, and as such the rapid resorption of the carrier poses enhanced difficulties. Examples of moderate or only slightly vascularized sites include, for example, transverse processes or other posterior elements of the spine, the diaphysis of long bones, in particular the mid diaphysis of the tibia, and cranial defects. An especially preferred use of paste or putty compositions of the invention is as an implant to promote arthrodesis between vertebrae in spinal fusions in humans or other mammals, including for example interbody, posterior and/or posterolateral fusion techniques.

Any suitable osteogenic material can be used in osteogenic methods and/or osteogenic materials of the invention, including for instance harvested autologous bone or other suitable osteogenic substances. In certain embodiments, the osteogenic substance can include a growth factor that is effective in inducing formation of bone. Desirably, the growth factor will be from a class of proteins known generally as bone morphogenic proteins (BMPs), and can in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in U.S. Pat. Nos. 5,965,403 and 6,331,612. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these Patents and applications are hereby incorporated herein by reference. Also useful in the present invention are heterodimers of the above and modified proteins or partial deletion products thereof. These proteins can be used individually or in mixtures of two or more. rhBMP-2 is preferred.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size and nature of the defect being treated, and the carrier and particular protein being employed. In certain embodiments, the amount of osteogenic protein to be delivered will be in a range of from about 0.05 to about 1.5 mg.

Other therapeutic growth factors or substances may also be used in implantable putties or other materials of the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-α and TGF-β. As well, other biologically-derived matrix materials such as demineralized bone matrix (DBM) may be incorporated into putties of the invention.

The osteogenic proteins or other biologically active agents to be used in the present invention can be provided in liquid formulations, for example buffered aqueous formulations. In certain embodiments, such formulations are mixed with, received upon and/or within, or otherwise combined with a dried implant material in order to prepare an osteogenic putty or other implantable material of the invention. On suitable rhBMP-2 formulation is available from Medtronic Sofamor Danek, Memphis, Tenn., with its INFUSE® Bone Graft product.

As further enhancements of the compositions of the present invention, those skilled in the art will readily appreciate that other osteogenic enhancing factors may be incorporated into the composition. Such additional factors include, but are not limited to autographic bone marrow, allographic bone marrow, transforming growth factor-beta, fibroblast growth factor, platelet derived growth factor, insulin-like growth factor, microglobulin-beta, antibiotics, antifungal agents, wetting agents, glycerol, steroids and non-steroidal anti-inflammatory compounds.

In addition, in accordance with other aspects of the invention, the putty or other implant materials of the invention can be incorporated in, on or around a load bearing implants such as spinal implants, hip implants (e.g. in or around implant stems and/or behind acetabular cups), knee implants (e.g. in or around stems). In inventive variants, an implant material of the invention can be incorporated in, on or around a load-bearing spinal implant device (e.g. having a compressive strength of at least about 10000 N) such as a fusion cage, dowel, or other device having a pocket, chamber or other cavity for containing an osteogenic material, and used in a spinal fusion such as an interbody fusion. One illustrative such use is in conjunction with a load-bearing interbody spinal spacer to achieve interbody fusion.

Osteogenic medical putty or other materials of the present invention can also comprise cells, including for instance progenitor and/or stem cells derived from embryonic or adult tissue sources and/or taken from culture. Illustratively, compositions of the invention can incorporate cells derived from blood, bone marrow, or other tissue sources from the patient to be treated (autologous cells) or from a suitable allogenic or xenogenic donor source. In certain embodiments of the invention, the implantable materials incorporate an enriched bone marrow fraction, prepared for example as described in US Patent Publication No. 2005/0130301 to McKay et al. published Jun. 16, 2005, publishing U.S. patent application Ser. No. 10/887,275 filed Jul. 8, 2004, which is hereby incorporated herein by reference in its entirety. Thus, implantable materials can incorporate a bone marrow fraction enriched in connective tissue growth components, that is prepared by centrifuging a biological sample (e.g. from the patient to be treated) to separate the sample into fractions including a fraction rich in connective tissue growth components. The fraction rich in connective tissue growth components can then be isolated from the separated sample, and incorporated into or otherwise combined with the implant material of the present invention, e.g. by using the fraction in or as the wetting medium for a three-dimensional implant body as discussed hereinabove.

The invention will now be more particularly described with reference to the following specific Example. It will be understood that this Example is illustrative and not limiting of the invention.

Example 1

Preparation of Inventive Putty with rhBMP-2

9 ml of a buffered aqueous solution of rhBMP-2 (1.5 mg/ml solution, as available with INFUSE® Bone Graft, Medtronic Sofamor Danek, Memphis, Tenn.) were added to a reservoir defined in a dried, porous body. The body was generally rectangular in shape, with a centrally-located rectangular reservoir. Amounts of the added aqueous solution pooled in the reservoir and were allowed time to soak into the body. The porous body had a volume of 18 cc and weighed approximately 3.8 grams. The dried, porous body had been prepared by casting and then lyophilizing an aqueous suspension of insoluble collagen fibers, acid soluble collagen, and ceramic granules, exhibited a porosity of about 85%, and was comprised of the following:

| Material | Wt % Solids |
| --- | --- |
| Biphasic CaP Granules* | 80% |
| Insoluble Collagen Fibers | 14% |
| Acid—Soluble Collagen | 6% |

*Mastergraft ® Ceramic Granules, biphasic calcium phosphate granules containing 85% tricalcium phosphate and 15% hydroxyapatite, particle size 0.5-1.6 mm, After soaking, the implant material and added rhBMP-2 solution were thoroughly mixed by kneading to prepare approximately 10 cc of an implantable putty material comprised about 70% by weight of water and containing about 0.3 g/cc biphasic calcium phosphate ceramic granules, 0.05 g/cc insoluble collagen fibers, 0.02 g/cc acid soluble collagen, and 1.5 mg/cc of rhBMP-2. The resulting osteogenic putty exhibited superior properties for handling and use. The putty retained its shape unless acted upon, and formed a malleable, cohesive, fibrous mass with entrained granules, that would elongate without breaking upon stretching.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A medical article, comprising: a three-dimensional body formed of an implantable material; said three-dimensional body being wettable with a biocompatible liquid; said three-dimensional body being disruptable upon wetting with the biocompatible liquid so as to form a wetted, disrupted implant material; and said three-dimensional body defining one or more reservoirs configured to receive and pool the biocompatible liquid, the medical article comprising 20% to 95% by weight of the biocompatible liquid.

2. The medical article of claim 1, wherein said one or more reservoirs have a combined volume of at least about 1 cc.

3. The medical article of claim 1, wherein said three-dimensional body defines at least one reservoir having an individual volume of at least 1 cc.

4. The medical article of claim 1, wherein the volumetric ratio of said reservoir(s) to said body is at least about 1:10.

5. The medical article of claim 1, wherein said body defines at least one reservoir having a volumetric ratio of at least 1:2 relative to said body.

6. The medical article of claim 1, wherein said implantable medical material comprises a resorbable polymer.

7. The medical article of claim 6, wherein the resorbable polymer is a natural polymer.

8. The medical article of claim 7, wherein the natural polymer is selected from the group consisting of collagen, elastin, hyaluronic acid, dermatan sulfate, chitin, chitosan, pectin, dextran, modified dextran, starch, and modified starch.

9. The medical article of claim 8, wherein the natural polymer is collagen.

10. The medical article of claim 9, wherein the implantable material comprises soluble collagen and insoluble collagen fibers.

11. The medical article of claim 1, wherein the implantable material comprises mineral.

12. The medical article of claim 10, wherein the implantable material also comprises mineral.

13. The medical article of claim 1, wherein said one or more reservoirs each comprise an open upper end, sidewalls, and a bottom surface.

14. The medical article of claim 1, wherein said body is porous.

15. The medical article of claim 1, wherein said body comprises lyophilized implantable material.

16. The medical article of claim 1, wherein said body exhibits substantially no shape memory.

17. The medical article of claim 1, wherein said body comprises a lyophilized collagenous structure that when dry is friable by hand and when wetted is susceptible to mixing by hand to prepare a conformable implant material.

18. The medical article of claim 17, wherein said body also comprises mineral particles.

19. The medical article of claim 1, wherein the one or more reservoirs comprises a ledge.

20. The medical article of claim 19, wherein the medical article comprises 40% to 80% by weight of the biocompatible liquid.

* * * * *